United States Patent [19]

Müller et al.

[11] Patent Number: 4,941,910
[45] Date of Patent: Jul. 17, 1990

[54] HERBICIDAL PYRIMIDINE DERIVATIVES

[75] Inventors: Klaus-Helmut Müller, Duesseldorf; Joachim Kluth; Klaus-Günther Tietjen, both of Langenfeld; Hans-Joachim Santel, Leverkusen; Robert R. Schmidt, Bergisch Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 321,941

[22] Filed: Mar. 10, 1989

[30] Foreign Application Priority Data

Mar. 16, 1988 [DE] Fed. Rep. of Germany ....... 3808739

[51] Int. Cl.$^5$ .................. A01N 43/54; C07D 239/47
[52] U.S. Cl. ........................................ 71/92; 544/317;
544/309; 544/310; 544/312; 544/314
[58] Field of Search ................. 71/92; 544/317, 309,
544/310, 312, 314

[56] References Cited

U.S. PATENT DOCUMENTS 3,974,162 8/1976 Santilli et al. .................... 544/317

FOREIGN PATENT DOCUMENTS 0139613 5/1985 European Pat. Off. .
2006145 10/1970 Fed. Rep. of Germany .

OTHER PUBLICATIONS

Sen et al., Chemical Abstracts, vol. 55, Entry 7423b (1961).
Wentrup Chemical Abstracts, vol. 74, Mar. 15, 1987, No. 11, p. 361 Entry 53726a.
Hurst Chemical Abstracts, vol. 100, 1984, pp. 646-647, Entry 139057a.

Primary Examiner—John M. Ford
Attorney, Agent, or Firm—Sprung Horn Kramer & Woods

[57] ABSTRACT

Herbicidal pyrimidine derivatives of the formula

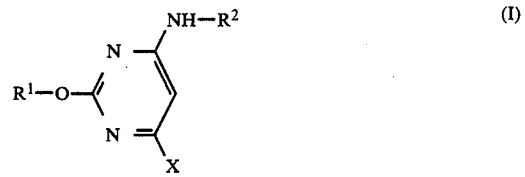

(I)

in which
$R^1$ stands for optionally substituted alkyl,
$R^2$ stands for an optionally substituted radical from the group consisting of alkyl, cycloalkyl, cycloalkylalkyl, aryl, aralkyl, heteroaryl and heteroarylalkyl, and stands for halogen, amino, cyanoamino or for an optionally substituted radical from the series comprising alkoxy, alkylthio, alkylamino and dialkylamino.

Intermediates of the formula

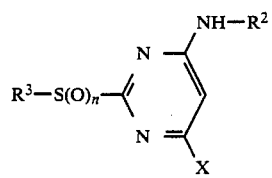

in which
$R^3$ is optionally substituted alkyl or benzyl, and n is 0 or 2,
are also new.

7 Claims, No Drawings

HERBICIDAL PYRIMIDINE DERIVATIVES

The invention relates to new pyrimidine derivatives, processes for their preparation and their use as herbicides.

It has been disclosed that certain pyrimidine derivatives, such as, for example, 2-amino-4-chloro-6-isopropylamino-pyrimidine, exhibit herbicidal properties (cf. DE-OS No. (German Published Specification) 2,006,145). However, the herbicidal action of the known pyrimidine derivatives is unsatisfactory at low application rates.

The new pyrimidine derivatives of the general formula (I)

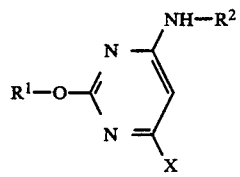  (I)

in which
- $R^1$ stands for optionally substituted alkyl,
- $R^2$ stands for an optionally substituted radical from the series comprising alkyl, cycloalkyl, cycloalkylalkyl, aryl, aralkyl, heteroaryl and heteroarylalkyl, and
- X stands for halogen, amino, cyanoamino or for an optionally substituted radical from the series comprising alkoxy, alkylthio, alkylamino and dialkylamino, have now been found.

Furthermore, it has been found that the new pyrimidine derivatives of the general formula (I) are obtained by a process in which (a) 2-alkylsulphonyl-pyrimidine derivatives of the general formula (II)

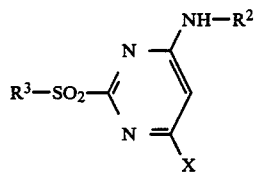  (II)

in which
- $R^2$ and X have the abovementioned meanings and
- $R^3$ stands for optionally substituted alkyl or benzyl, are reacted with metal alkoxides of the general formula (III)

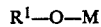 $R^1$—O—M  (III)

in which
- $R^1$ has the abovementioned meaning and
- M stands for a metal equivalent, if appropriate in the presence of a diluent, or (b) 4-halogeno-pyrimidine derivatives of the general formula (Ia)

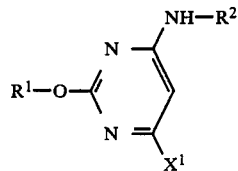  (Ia)

in which
- $R^1$ and $R^2$ have the abovementioned meanings and
- $X^1$ stands for halogen, are reacted with compounds of the general formula (IV)

 $M^1$—X  (IV)

in which
- X has the abovementioned meaning and
- $M^1$ stands for hydrogen or a metal equivalent, if appropriate in the presence of an acid acceptor and if appropriate in the presence of a diluent, or 4-halogeno-pyrimidine derivatives of the general formula (V)

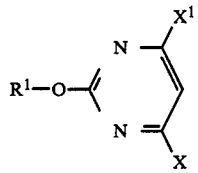  (V)

in which
- $R^1$, X and $X^1$ have the abovementioned meanings, are reacted with amino compounds of the general formula (VI)

 $H_2N$—$R^2$  (VI)

in which
- $R^2$ has the abovementioned meaning, if appropriate in the presence of an acid acceptor and if appropriate in the presence of a diluent.

The new pyrimidine derivatives of the general formula (I) are distinguished by a powerful herbicidal activity.

Surprisingly, the compounds of the general formula (I) according to the invention show a considerably more powerful action against weeds than known compounds which have a similar structure and range of action, while having a good selectivity in crop plants.

The invention preferably relates to compounds of the formula (I) in which $R^1$ stands for $C_1$–$C_6$-alkyl which is optionally substituted by fluorine, chlorine, bromine, $C_1$–$C_4$-alkoxy (which is optionally substituted by fluorine and/or chlorine), $C_1$–$C_4$-alkoxy-$C_1$–$C_4$-alkoxy, $C_1$–$C_4$-alkylthio, $C_1$–$C_4$-alkylamino or di($C_1$–$C_4$-alkyl)-amino, $R^2$ stands for $C_1$–$C_6$-alkyl which is optionally substituted by fluorine, chlorine, $C_1$–$C_4$-alkoxy, $C_1$–$C_4$-alkylthio, $C_1$–$C_4$-alkylamino or di($C_1$–$C_4$-alkyl)-amino, for $C_3$–$C_6$-cycloalkyl or $C_3$–$C_6$-cycloalkyl-$C_1$–$C_3$-alkyl which are optionally substituted by fluorine, chlorine, bromine and/or $C_1$–$C_4$-alkyl, or for a grouping from the series comprising phenyl, naphthyl, phenyl-$C_1$–$C_4$-alkyl, naphthyl-$C_1$–$C_4$-alkyl, pyridyl, pyridyl-$C_1$-$C_4$-alkyl, quinolinyl, quinolinyl-$C_1$-$C_4$-alkyl, isoquinolinyl, isoquinolinyl-$C_1$-$C_4$-alkyl, pyrimidinyl, pyrimidinyl-$C_1$-$C_4$-alkyl, furyl, furylmethyl, thienyl, thienylmethyl, pyrrolyl, pyrrolyl-$C_1$-$C_4$-alkyl, pyrazolyl, pyrazolyl-$C_1$-$C_4$-alkyl, imidazolyl and imidazolyl-$C_1$-$C_4$-alkyl which is optionally substituted by fluorine, chlorine, bromine, iodine, cyano, nitro, $C_1$-$C_4$-alkyl (which is optionally substituted by fluorine and/or chlorine), $C_1$-$C_4$-alkoxy or $C_1$-$C_2$-alkylenedioxy (which are optionally substituted by fluorine and/or chlorine), $C_1$-$C_4$-alkylthio, $C_1$-$C_4$-alkylsulphinyl or $C_1$-$C_4$-alkylsulphonyl (which are optionally substituted by fluorine and/or chlorine), di-($C_1$-$C_2$-alkyl)-amino and/or by $C_1$-$C_4$-alkoxy-carbonyl, and X stands for fluorine, chlorine, bromine, amino, cyanoamino or for a radical from the series comprising $C_1$-$C_4$-alkoxy, $C_1$-$C_4$-alkylthio, $C_1$-$C_4$-alkylamino and di-($C_1$-$C_4$-alkyl)-amino which is optionally substituted by fluorine, chlorine, bromine, $C_1$-$C_4$-alkoxy, $C_1$-$C_4$-alkylthio, $C_1$-$C_4$-alkylamino or di-($C_1$-$C_4$-alkyl)-amino.

In particular, the invention relates to compounds of the formula (I) in which $R^1$ stands for $C_1$-$C_4$-alkyl which is optionally substituted by $C_1$-$C_3$-alkoxy (which is optionally substituted by fluorine) or by $C_1$-$C_3$-alkoxy-$C_1$-$C_3$-alkoxy, $R^2$ stands for $C_1$-$C_4$-alkyl, $C_3$-$C_6$-cycloalkyl, $C_3$-$C_6$-cycloalkyl-methyl, for phenyl or naphthyl which are optionally substituted by fluorine, chlorine, bromine, cyano, nitro, methyl, ethyl, trifluoromethyl, methoxy and/or ethoxy, for phenyl-$C_1$-$C_3$-alkyl or naphthyl-$C_1$-$C_3$-alkyl which are optionally substituted by fluorine, chlorine, bromine, cyano, nitro, methyl, ethyl, trifluoromethyl, methoxy and/or ethoxy, for pyridyl or pyridylmethyl which are optionally substituted by fluorine, chlorine, bromine, cyano, nitro, methyl, ethyl, methoxy and/or ethoxy or for furyl or furylmethyl which are optionally substituted by fluorine, chlorine, bromine, methyl and/or ethyl, and X stands for chlorine, methoxy, ethoxy, methylthio or ethylthio.

Very particularly preferred compounds of the formula (I) are those in which $R^1$ stands for $C_1$-$C_2$-alkoxy-$C_1$-$C_3$-alkyl, $R^2$ stands for (R/S)- or (S)-1-phenylethyl which are optionally substituted by fluorine, chlorine, bromine or methyl and X stands for chlorine.

If, for example, 4-chloro-6-isopropylamino-2-methylsulphonyl-pyrimidine and the potassium salt of 3-methoxy-propanol are used as starting substances, the course of the reaction in process (a) according to the invention can be outlined by the following equation:

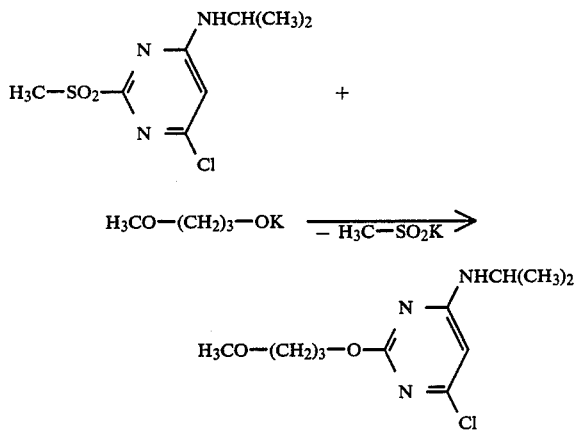

If, for example, 4-chloro-6-benzylamino-2-(2-ethoxyethoxy)-pyrimidine and sodium ethoxide are used as starting substances, the course of the reaction in process (b) according to the invention can be outlined by the following equation:

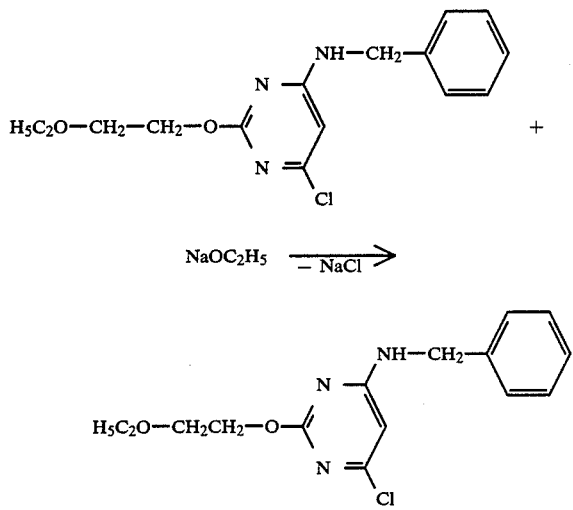

If, for example, 2-(2-ethoxy-2-ethoxy-ethoxy)-4,6-dichloropyrimidine and 2-(4-chloro-phenyl)-ethylamine are used as starting substances, the course of the reaction in process (c) according to the invention can be outlined by the following equation:

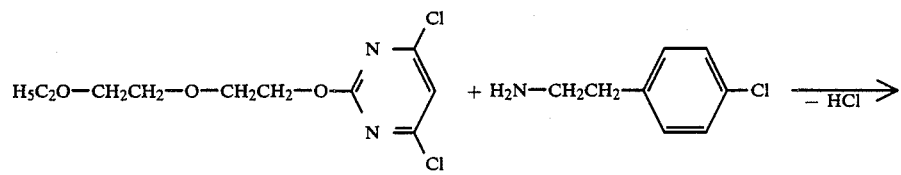

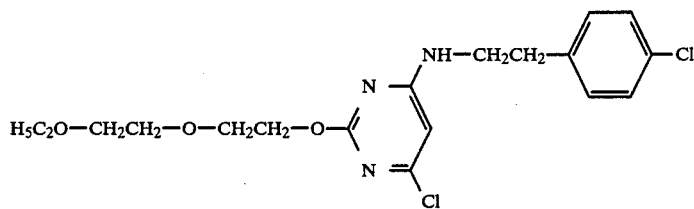

Formula (II) provides a general definition of the 2-alkyl-sulphonyl-pyrimidine derivatives to be used as starting substances in process (a) according to the invention. In formula (II), $R^2$ and X preferably, or in particular, or very particularly preferentially, have those meanings which have already been indicated above in context with the description of the compounds of the formula (I) as being preferred, or particularly preferred, or very particularly preferred, for $R^2$ and X, and $R^3$ preferably stands for $C_1$-$C_4$-alkyl, in particular for methyl.

Examples of the starting substances of the formula (II) are listed in Table 1 below.

TABLE 1

Examples of the starting substances of the formula (II)

$$R^3-SO_2-\underset{N}{\underset{\|}{\overset{NH-R^2}{\overset{N}{\bigcirc}}}}-X \quad (II)$$

| $R^2$ | $R^3$ | X |
|---|---|---|
| $-CH_2-C_6H_5$ | $CH_3$ | Cl |
| $C_2H_5$ | $CH_3$ | Cl |
| $C_3H_7$ | $CH_3$ | Cl |
| $CH(CH_3)_2$ | $CH_3$ | Cl |
| $C_4H_9$ | $CH_3$ | Cl |
| $CH_2CH(CH_3)_2$ | $CH_3$ | Cl |
| $CHCH_2CH_3$ \| $CH_3$ | $CH_3$ | Cl |
| $C(CH_3)_3$ | $CH_3$ | Cl |
| cyclopropyl (-CH<CH_2-CH_2) | $CH_3$ | Cl |
| cyclopentyl | $CH_3$ | Cl |
| cyclohexyl (-H) | $CH_3$ | Cl |
| $-CH_2$-cyclopentyl | $CH_3$ | Cl |

TABLE 1-continued

Examples of the starting substances of the formula (II)

$$R^3-SO_2-\underset{N}{\underset{\|}{\overset{NH-R^2}{\overset{N}{\bigcirc}}}}-X \quad (II)$$

| $R^2$ | $R^3$ | X |
|---|---|---|
| phenyl | $CH_3$ | Cl |
| $-C_6H_4-CH_3$ (p-tolyl) | $CH_3$ | Cl |
| (R/S)-$-CH(CH_3)-C_6H_5$ | $CH_3$ | Cl |
| (R)-$-CH(CH_3)-C_6H_5$ | $CH_3$ | Cl |
| (S)-$-CH(CH_3)-C_6H_5$ | $CH_3$ | Cl |
| $-CH_2-C_6H_4-CH_3$ | $CH_3$ | Cl |
| $-CH_2-C_6H_4-Cl$ | $CH_3$ | Cl |
| $-CH_2$-(2-pyridyl) | $CH_3$ | Cl |
| $-CH_2$-(3-pyridyl) | $CH_3$ | Cl |

TABLE 1-continued

Examples of the starting substances of the formula (II)

$$\begin{array}{c} \text{NH}-\text{R}^2 \\ \text{N} \\ \text{R}^3-\text{SO}_2 \\ \text{N} \\ \text{X} \end{array} \quad (II)$$

| $R^2$ | $R^3$ | X |
|---|---|---|
| —CH$_2$—(2-chloropyridin-5-yl) | CH$_3$ | Cl |
| —CH$_2$—C$_6$H$_4$—OCH$_3$ (4-) | CH$_3$ | Cl |
| —CH$_2$—C$_6$H$_4$—Br (4-) | CH$_3$ | Cl |
| —CH$_2$—C$_6$H$_4$—CF$_3$ (4-) | CH$_3$ | Cl |
| (R/S)—CH(CH$_3$)—C$_6$H$_4$—Cl (4-) | CH$_3$ | Cl |
| (R)—CH(CH$_3$)—C$_6$H$_4$—Cl (4-) | CH$_3$ | Cl |
| (S)—CH(CH$_3$)—C$_6$H$_4$—Cl (4-) | CH$_3$ | Cl |
| —CH$_2$—C$_6$H$_4$—C(CH$_3$)$_3$ (4-) | CH$_3$ | Cl |
| —CH$_2$—(3,4-methylenedioxyphenyl) | CH$_3$ | Cl |
| (R/S)—CH(CH$_3$)—C$_6$H$_3$—Cl$_2$ (3,4-) | CH$_3$ | Cl |
| (S)—CH(CH$_3$)—C$_6$H$_3$—Cl$_2$ (3,4-) | CH$_3$ | Cl |
| —CH$_2$—C$_6$H$_4$—F (4-) | CH$_3$ | Cl |
| (R/S)—CH(CH$_3$)—C$_6$H$_4$—F (4-) | CH$_3$ | Cl |
| (S)—CH(CH$_3$)—C$_6$H$_4$—F (4-) | CH$_3$ | Cl |
| —CH$_2$CH$_2$—C$_6$H$_5$ | CH$_3$ | Cl |
| —CH$_2$—(furan-2-yl) | CH$_3$ | Cl |
| (S)—CH(CH$_3$)—C$_6$H$_5$ | CH$_3$ | OCH$_3$ |

The starting substances of the formula (II) were hitherto not known from the literature. The new 2-alkyl-sulphonyl-pyrimidine derivatives of the general formula (II) are obtained when corresponding 2-alkylthio-pyrimidine derivatives of the general formula (VII)

$$\begin{array}{c} \text{NH}-\text{R}^2 \\ \text{N} \\ \text{R}^3-\text{S} \\ \text{N} \\ \text{X} \end{array} \quad (VII)$$

in which

R$^2$, R$^3$ and X have the abovementioned meanings, are reacted with oxidizing agents, such as, for example, hydrogen peroxide, at temperatures between 0° C. and 50° C., if appropriate in the presence of catalysts, such as, for example, ammonium molybdate and formic acid, and if appropriate in the presence of diluents, such as, for example, methylene chloride, and the reaction product is worked up by customary methods.

In formular (VII), R$^2$ and X preferably, or in particular, or very particularly preferentially, have those meanings which have already been mentioned above in connection with the description of the compounds of the formula (I) according to the invention as being preferred, or particularly preferred, or very particularly preferred, for $R^2$ and X, and $R^3$ preferably stands for $C_1$-$C_4$-alkyl, in particular for methyl.

Examples of meanings of $R^2$, $R^3$ and X have already been mentioned in Table 1.

The intermediates of the formula (VII) were hitherto not known from the literature. The new 2-alkylthio-pyrimidine derivatives of the general formula (VII) are obtained when 2-alkylthio-4,6-dichloro-pyrimidine derivatives of the general formula (VIII)

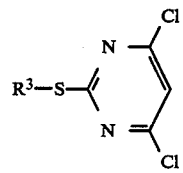
(VIII)

in which
$R^3$ has the abovementioned meaning,
are reacted with amino compounds of the general formula (VI)

 (VI)

in which
$R^2$ has the abovementioned meaning,
and, if appropriate, the reaction product is then reacted with compounds of the general formula (IV)

 (IV)

in which
$M^1$ and X have the abovementioned meanings,
at temperatures between 0° C. and 150° C., if appropriate in the presence of acid acceptors, such as, for example, triethylamine, and if appropriate in the presence of diluents, such as, for example, toluene, tetrahydrofuran or dioxane, and the product is worked up by customary methods.

The compounds of the formula (VIII) are known and/or can be prepared by processes known per se (cf. J. Org. Chem. 26 (1961), 792; U.S. Pat. No. 4,199,583).

The compounds of the formulas (VI) and (IV) are known chemicals for synthesis.

Formula (III) provides a general definition of the metal alkoxides also to be used as starting substances in the process according to the invention. In formula (III), $R^1$ preferably, or in particular, or very particularly preferentially has the meaning which has already been mentioned in context with the description of the compounds of the formula (I) according to the invention as being preferred, or particularly preferred, or very particularly preferred, and M preferably stands for sodium or potassium.

Examples of the starting substances of the formula (III) which may be mentioned are the sodium salts and the potassium salts of 2-methoxy-ethanol, 2-ethoxyethanol, 3-methoxy-propanol, 2-methoxy-propanol, 3-ethoxypropanol, 2-(2-methoxy-ethoxy)-ethanol, 2-(2-ethoxy-ethoxy)-ethanol and 2-(2,2,2-trifluoroethoxy)-ethanol.

The compounds of the formula (III) are known and/or can be prepared in a simple manner from corresponding alcohols and suitable metals, such as, for example, sodium or potassium.

Formula (Ia) provides a general definition of the 4-halogeno-pyrimidine derivatives to be used as starting substances in process (b) according to the invention. In formula (Ia), $R^1$ and $R^2$ preferably, or in particular, or very particularly preferably, have those meanings which have already been mentioned in context with the description of the compounds of the formula (I) according to the invention as being preferred, or particularly preferred, or very particularly preferred, for $R^1$ and $R^2$, and $X^1$ preferably stands for chlorine.

Examples of the starting substances of the formula (Ia) are listed in Table 2 below.

TABLE 2

Examples of the starting substances of the formula (Ia)

(Ia)

| $R^1$ | $R^2$ | $X^1$ |
|---|---|---|
| $-CH_2CH_2-OCH_3$ | $-CH_2-\phi$ | Cl |
| $-CH_2CH_2-OC_2H_5$ | $-CH_2-\phi$ | Cl |
| $-(CH_2)_3-OCH_3$ | $-CH_2-\phi$ | Cl |
| $-CH_2CH_2-OCH_3$ | $C_2H_5$ | Cl |
| $-CH(CH_3)-CH_2-OCH_3$ | $C_3H_7$ | Cl |
| $-CH_2CH_2-OCH_3$ | $CH(CH_3)_2$ | Cl |
| $-CH_2-OC_2H_5$ | $C_4H_9$ | Cl |
| $-CH_2CH_2-OCH_3$ | cyclopropyl-CH | Cl |
| $-CH_2CH_2-OC_2H_5$ | cyclopentyl | Cl |
| $-CH_2CH_2-OCH_3$ | $-CH_2-$cyclohexyl-H | Cl |
| $-CH_2CH_2-OC_2H_5$ | $CH_2CH(CH_3)_2$ | Cl |
| $-CH_2CH_2-OCH_3$ | (R/S)-CH(CH_3)-$\phi$ | Cl |

TABLE 2-continued

Examples of the starting substances of the formula (Ia)

$$\text{R}^1-\text{O}-\underset{\underset{X^1}{\overset{N}{\parallel}}}{\overset{NH-R^2}{\underset{N}{\bigcirc}}}\quad (Ia)$$

| $R^1$ | $R^2$ | $X^1$ |
|---|---|---|
| —CH₂CH₂—OCH₃ | (R)—CH(CH₃)—C₆H₅ | Cl |
| —CH₂CH₂—OCH₃ | (S)—CH(CH₃)—C₆H₅ | Cl |
| —CH₂CH₂—OC₂H₅ | (R/S)—CH(CH₃)—C₆H₅ | Cl |
| —CH₂CH₂—OCH₃ | (S)—CH(CH₃)—C₆H₄—Cl (4) | Cl |
| —CH₂CH₂—OC₂H₅ | (S)—CH(CH₃)—C₆H₅ | Cl |
| —CH₂CH₂—OCH₃ | (R/S)—CH(CH₃)—C₆H₄—Cl (4) | Cl |
| —CH₂CH₂—OCH₃ | —CH₂—C₆H₄—CH₃ (4) | Cl |
| —CH₂CH₂—OC₂H₅ | —CH₂—C₆H₄—Cl (4) | Cl |
| —CH₂CH₂—OCH₃ | —CH₂—(2-pyridyl) | Cl |
| —CH₂CH₂—OC₂H₅ | —CH₂—(3-pyridyl) | Cl |
| —CH₂CH₂—OCH₃ | —CH₂—(6-chloro-3-pyridyl) | Cl |
| —CH₂CH₂—OC₂H₅ | —CH₂—C₆H₄—OCH₃ (4) | Cl |
| —CH₂CH₂—OCH₃ | —CH₂—C₆H₄—Br (4) | Cl |
| —CH₂CH₂—OC₂H₅ | —CH₂—C₆H₄—CF₃ (4) | Cl |
| —(CH₂)₃—OCH₃ | (R/S)—CH(CH₃)—C₆H₅ | Cl |
| —(CH₂)₃—OCH₃ | (S)—CH(CH₃)—C₆H₅ | Cl |
| —CH₂CH₂—OC₂H₅ | (S)—CH(CH₃)—C₆H₄—Cl (4) | Cl |
| —CH₂CH₂—OC₂H₅ | (R/S)—CH(CH₃)—C₆H₄—Cl (4) | Cl |
| —CH₂CH₂—OCH₃ | —CH₂—C₆H₄—C(CH₃)₃ (4) | Cl |
| —CH₂CH₂—OC₂H₅ | —CH₂—C₆H₃(3,4-OCH₂O—) (methylenedioxy) | Cl |
| —CH₂CH₂—OCH₃ | (R/S)—CH₂—C₆H₃—Cl₂ (3,4) | Cl |

TABLE 2-continued
Examples of the starting substances of the formula (Ia)

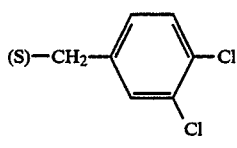

(Ia)

| $R^1$ | $R^2$ | $X^1$ |
|---|---|---|
| —$CH_2CH_2$—$OC_2H_5$ | (S)—$CH_2$—[3,4-diClPh] | Cl |
| —$(CH_2)_3$—$OCH_3$ | —$CH_2$—[4-FPh] | Cl |
| —$CH_2CH_2$—$OCH_3$ | (R/S)—$CH(CH_3)$—[4-FPh] | Cl |
| —$CH_2CH_2$—$OC_2H_5$ | (S)—$CH(CH_3)$—[4-FPh] | Cl |
| —$CH_2CH_2$—$OCH_3$ | —$CH_2CH_2$—[Ph] | Cl |
| —$CH_2CH_2$—$OC_2H_5$ | —$CH_2$—[furyl] | Cl |
| —$CH_2CH_2$—$OCH_2$—$CF_3$ | (S)—$CH(CH_3)$—[4-ClPh] | Cl |
| —$CH_2CH_2$—$OC_2H_4$—$OC_2H_5$ | (S)—$CH(CH_3)$—[3,4-diClPh] | F |
| —$CH_2CH_2$—$OC_2H_4$—$OCH_3$ | (S)—$CH(CH_3)$—[3,4-diClPh] | F |

The starting substances of the formula Ia) are also active compounds according to the invention which are included in the definition of formula (I). They can be prepared by process (a) according to the invention.

Formula (IV) provides a general definition of the compounds also to be employed as starting substances in process (b). In formula (IV), X preferably, or in particular, or very particularly preferentially, has the meaning which has already been mentioned in context with the description of the compounds of the formula (I) according to the invention as being preferred, or particularly preferred, or very particularly preferred, for X, and $M^1$ preferably stands for hydrogen, lithium, sodium or potassium, in particular for sodium or potassium.

Examples of starting substances of the formula (IV) which may be mentioned are: sodium fluoride, potassium fluoride, sodium bromide, potassium bromide, sodium iodide, potassium iodide, ammonia, sodium amide, potassium amide, methanol, ethanol, propanol, isopropanol, butanol and 2-methyl-propanol and their sodium and potassium salts, methanethiol, ethanethiol, propanethiol, 1-methyl-ethanethiol, butanethiol, 1-methyl-propanethiol and 2-methyl-propanethiol and their sodium and potassium salts, methylamine, ethylamine, propylamine, isopropylamine, butylamine, isobutylamine, dimethylamine, diethylamine and cyanamide.

The starting substances of the formula (IV) are known chemicals for synthesis.

Formula (V) provides a general definition of the 4-halogeno-pyrimidine derivatives to be used as starting substances in process (c) according to the invention.

In formula (V), $R^1$ and X preferably, or in particular, have those meanings which have already been preferentially mentioned above, or mentioned above as particularly preferred, for $R^1$ and X in connection with the description of the compounds of the formula (I) according to the invention, and $X^1$ preferably stands for chlorine.

Examples of the starting substances of the formula (V) which may be mentioned are: 2-(2-methoxy-ethoxy)-, 2-(2-ethoxy-ethoxy)-, 2-(3-methoxy- propoxy)-, 2-(3-ethoxy-propoxy)-, 2-(2-methoxy-propoxy)and 2-(2-ethoxy-propoxy)-4,6-dichloro-pyrimidine.

The starting substances of the formula (V) are known and/or can be prepared by methods known per se, starting from, for example, 2,4,6-trichloro-pyrimidine or 2-methylsulphonyl-4,6-dichloro-pyrimidine (cf., for example, Liebig's Ann. Chem. 1975, p. 1113 et seq. and Austral. J. Chem. Vol. 18, p. 199 et seq.).

Formula (VI) provides a general definition of the amino compounds also to be used as starting substances in process (c) according to the invention.

In formula (VI), $R^2$ preferably, or in particular, has the meaning which has already been preferentially mentioned above, or mentioned above as particularly preferred, for $R^2$ in connection with the description of the compounds of the formula (I) according to the invention.

Examples of the starting substances of the formula (VI) which may be mentioned are:

Methylamine, ethylamine, propylamine, isopropylamine, butylamine, isobutylamine, cyclopropylamine, cyclobutylamine, cyclopentylamine, cyclohexylamine, cyclopentylmethylamine, cyclohexylmethylamine, benzylamine, 1-phenyl-ethylamine, 1-(4-fluoro-phenyl)-ethylamine, 1-(4-chloro-phenyl)-ethylamine, 1-(4-bromo-phenyl)-ethylamine, 1-(4-methyl-phenyl)-ethylamine, 1-(4-trifluoromethyl- phenyl)-ethylamine, 1-(4-methoxy-phenyl)-ethylamine and 1-(3,4-dichloro-phenyl)-ethylamine.

The starting substances of the formula (VI) are known chemicals for synthesis.

Process (a) according to the invention is preferably carried out in the presence of a diluent. Suitable diluents are virtually all inert organic solvents, in particular, however, aprotic polar solvents. These include chlorinated hydrocarbons, such as, for example, methylene chloride, chloroform or chlorobenzene, ketones, such as, for example, acetone, methyl ethyl ketone, methyl isopropyl ketone and methyl isobutyl ketone, nitriles, such as, for example, acetonitrile and propionitrile, ethers, such as, for example, diethyl ether, diisopropyl ether, dimethoxyethane, tetrahydrofuran and dioxane, amides, such as, for example, dimethylformamide and dimethylacetamide, and also dimethyl sulphoxide and sulpholane.

The following aprotic polar solvents are particularly preferred from the group mentioned: dimethylformamide, dimethylacetamide, acetonitrile and propionitrile.

When carrying out the process (a) according to the invention, the reaction temperatures can be varied within a relatively wide range. In general, the process is carried out at temperatures between 0° C. and 150° C., preferably at temperatures between 10° C. and 100° C. Process (a) is generally carried out under normal pressure.

For carrying out process (a) according to the invention, between 1 and 10 moles, preferably between 1 and 5 moles, of metal alkoxide of the formula (III) are employed per mole of 2-alkylsulphonyl-pyrimidine derivative of the formula (II). The reactants are usually combined at room temperature or with gentle cooling, and the mixture is stirred until the reaction is complete. Working up can be carried out by customary methods. For example, the mixture is concentrated, if appropriate, and then extracted by shaking with water and a virtually water-immiscible organic solvent, such as, for example, methylene chloride, and the organic phase is dried, if appropriate, and filtered. The solvent is carefully removed from the filtrate by distillation under reduced pressure. The residue remaining contains essentially the product of the formula (I).

Process (b) according to the invention is preferably carried out using diluents. Suitable diluents in this process are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

Acid acceptors which can be employed in process (b) according to the invention are all acid-binding agents which can be used in reactions of this type. Alkali metal carbonates and alkali metal alkoxides, such as sodium carbonate, potassium carbonate, sodium tert-butoxide and potassium tert-butoxide, furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diaza- bicyclo-[2,2,2]-octane (DABCO) are preferably suitable.

When carrying out process (b) according to the invention, the reaction temperatures can be varied within a relatively wide range. In general, the process is carried out at temperatures between 0° C. and 150° C., preferably at temperatures between 10° C. and 100° C.

In general, process (b) according to the invention is carried out under normal pressure. However, it is also possible for the process to be carried out under increased or reduced pressure.

For carrying out process (b) according to the invention, between 1 and 10 moles, preferably between 1 and 5 moles, of compound of the formula (IV) are employed per mole of 4-halogeno-pyrimidine derivative of the formula (Ia). The reaction can be carried out, and the reaction products can be worked up, as indicated in process (a).

Process (c) according to the invention is preferably carried out using diluents. Possible diluents are in particular those organic solvents which have been mentioned above in connection with the description of process (b) according to the invention.

Acid acceptors which can be employed in process (c) according to the invention are all acid-binding agents which can customarily be employed for reactions of this type. Possible acid acceptors are preferably those which have been mentioned above in connection with the description of process (b) according to the invention.

When carrying out process (c) according to the invention, the reaction temperatures can be varied within a relatively wide range. In general, the process is carried out at temperatures between 0° C. and 150° C., preferably at temperatures between 10° C. and 100° C.

Process (c) according to the invention is generally carried out under atmospheric pressure. However, it is also possible for the process to be carried out under increased or reduced pressure.

For carrying out process (c) according to the invention, between 1 and 3 moles, preferably between 1 and 2 moles, of amino compound of the formula (VI) are generally employed per mole of 4-halogeno-pyrimidine derivative of the formula (V). The reaction can be carried out, and the reaction products can be worked up, as has been indicated in process (a).

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are suitable for selectively combating monocotyledon and dicotyledon weeds, in particular in monocotyledon crops, preferably by the post-emergence method.

Some of the compounds according to the invention also show a fungicidal action, for example against powdery mildew on cucumbers or against Pyricularia oryzae on rice.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the caseof the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as poly-oxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used, for combating weeds, as mixtures with known herbicides, finished formulations or tank mixes being possible.

Suitable components for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethyl-urea (METABENZTHIAZURON) for combating weeds in cereals; 4-amino-3-methyl-6-phenyl-1,2,4-triazin-5(4H)-one (METAMITRON) for combating weeds in sugarbeets and 4-amino-6-(1,1-dimethylethyl)-3-methylthio-1,2,4-triazin-5(4H)-one (METRIBUZIN) for combating weeds in soy beans; furthermore also 2,4-dichlorophenoxyacetic acid (2,4-D); 4-(2,4-dichlorophenoxy)-butyric acid (2,4-DB); 2,4-dichlorophenoxypropionic acid (2,4-DP); 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxy-benzonitrile (BROMOXYNIL); 2-chloro-N-{[(4-methoxy-6-methyl-1,3,5-triazin-2-yl)-amino]-carbonyl}benzenesulphonamide CHLORSULFURON); N,N-dimethyl-N'-(3-chloro-4-methylphenyl)-urea (CHLORTOLURON); 2-[4-(2,4-dichlorophenoxy)-phenoxy]-propionic acid, its methyl ester or its ethyl ester (DICLOFOP); 4-amino-6-t-butyl-3-ethylthio-1,2,4-triazin-5(4H)-one (ETHIOZIN); 2-{4-[(6-chloro-2-benzoxazolyl)-oxy]-phenoxy}-propanoic acid, its methyl ester or its ethyl ester (FENOXAPROP); methyl 2-[4,5-dihydro-4-methyl-4-(1-methylethyl)-5-oxo-1H-imidazol-2-yl]4(5)-methylbenzoate (IMAZAMETHABENZ); 3,5-diiodo-4-hydroxybenzonitrile (IOXYNIL); N,N-dimethyl-N'-(4-isopropylphenyl)urea (ISOPROTURON); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-{[[((4-methoxy-6-methyl-1,3,5-triazin-2-yl)amino)-carbonyl]-amino]-sulphonyl}-benzoic acid or its methyl ester (METSULFURON); N-(1-ethylpropyl)-3,4-dimethyl-2,6-dinitroaniline (PENDIMETHALIN); 0-(6-chloro-3-phenyl- pyridazin-4-yl) S- octyl-thiocarbonate (PYRIDATE); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulphonyl]-thiophene-2-carboxylate (THIAMETURON), and 3,5,6-trichloro-2-pyridyloxyacetic acid (TRICLOPYR). Surprisingly, some of these mixtures also show synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.01 and 15 kg of active compound per hectare of soil surface, preferably between 0.05 and 10 kg per ha.

The preparation and use of the active compounds according to the invention can be seen from the following examples.

PREPARATION EXAMPLES

EXAMPLE 1

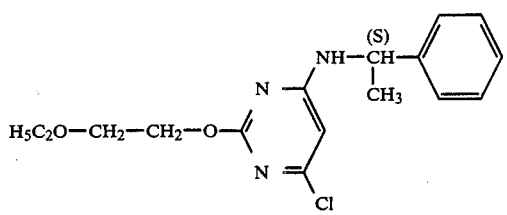

(Process (A))

A mixture of 3.3 g (0.011 mol) of (S)-4-chloro-2-methylsulphonyl-6-(1-phenyl-ethylamino)-pyrimidine, 4.0 g (0.036 mol) of the sodium salt of 2-ethoxy-ethanol and 50 ml of acetonitrile is stirred for 12 hours at 20° C. The mixture is concentrated and extracted by shaking with methylene chloride/water, and the organic phase is dried over sodium sulphate and filtered. The solvent is carefully removed from the filtrate by distillation in a water pump vacuum.

2.9 g (85% of theory) of (S)-4-chloro-2-(2-ethoxy-ethoxy)-6-(1-phenyl-ethylamino)-pyrimidine are obtained as a pale brown oily residue.

$^1$H-NMR (CDCl$_3$, 300 MHz), $\delta = 1.20$ (t, CH$_2$CH$_3$); 1.55 (d, CHCH$_3$); 3.55 (q, CH$_2$CH$_3$); 3.71 and 4.38 (m, OCH$_2$CH$_2$O).

The compounds of the formula (I) which are listed in Table 3 below can be prepared in analogy to Example 1 or following the general description of the preparation processes according to the invention.

TABLE 3

Examples of the compounds of the formula (I)

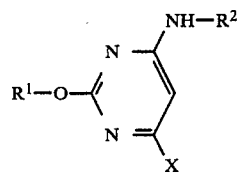

| Ex. No. | R$^1$ | R$^2$ | X | Physical constants |
|---|---|---|---|---|
| 2 | —CH$_2$CH$_2$—OC$_2$H$_5$ | —CH(CH$_2$)(CH$_2$) (cyclopropyl) | Cl | 76° C. |
| 3 | —CH$_2$CH$_2$—OC$_2$H$_5$ | —C$_6$H$_{11}$ (cyclohexyl, H) | Cl | NMR spectrum* |
| 4 | —CH$_2$CH$_2$—OCH$_3$ | (S)—CH(CH$_3$)—C$_6$H$_5$ | Cl | n$_D^{22}$ = 1.5680 |
| 5 | —CH$_2$CH$_2$—OCH$_3$ | (R/S)—CH(CH$_3$)—C$_6$H$_5$ | Cl | |

TABLE 3-continued
Examples of the compounds of the formula (I)

(I)

$$\text{R}^1-\text{O}-\underset{\underset{X}{\|}}{\overset{\overset{NH-R^2}{|}}{\text{pyrimidine}}}$$

| Ex. No. | $R^1$ | $R^2$ | X | Physical constants |
|---|---|---|---|---|
| 6 | —CH₂CH₂—OC₂H₅ | (R/S)—CH(CH₃)—C₆H₅ | Cl | |
| 7 | —(CH₂)₃—OCH₃ | (S)—CH(CH₃)—C₆H₅ | Cl | |
| 8 | —C₂H₄—O—C₂H₄—OCH₃ | (S)—CH(CH₃)—C₆H₅ | Cl | $n_D^{22} = 1.5582$ |
| 9 | —C₂H₄—O—C₂H₄—OC₂H₅ | (S)—CH(CH₃)—C₆H₅ | Cl | $n_D^{21} = 1.5419$ |
| 10 | —C₂H₄—OCH₂—CF₃ | (S)—CH(CH₃)—C₆H₅ | Cl | $n_D^{22} = 1.4999$ |
| 11 | —CH₂CH₂—OCH₃ | (S)—CH(CH₃)—C₆H₅ | OCH₃ | $n_D^{23} = 1.5604$ |
| 12 | —CH₂CH₂—O—C₂H₄—OCH₃ | (S)—CH(CH₃)—C₆H₅ | OCH₃ | $n_D^{23} = 1.5456$ |

*¹H—NMR in Example 3 (CDCl₃, 300 MHz); δ = 1.21 (t, CH₃); 1.13–2.05 (m, C₆H₁₁), 3.57 (q, OCH₂CH₃); 3.76 (m, OCH₂); 4.41 (m, OCH₂); 5.06 (s, NH); 5.98 (s, CH).

STARTING SUBSTANCES OF THE FORMULA (II)

EXAMPLE (II-1)

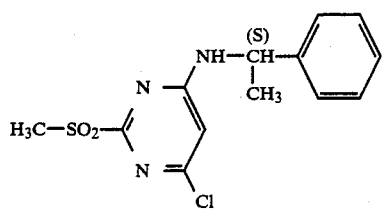

5.4 g (0.019 mol) of (S)-4-chloro-2-methylthio-6-(1-phenyl-ethylamino)-pyrimidine are dissolved in 100 ml of methylene chloride. 2 g of formic acid and 0.1 g of ammonium molybdate are added, and 6.0 g of 35% strength aqueous hydrogen peroxide solution are added dropwise to the stirred reaction mixture. The mixture is stirred for 12 hours at 20° C., and the organic phase is separated off, washed with highly diluted sodium hydrogen sulphite solution, dried over sodium sulphate and filtered. The solvent is carefully removed from the filtrate by distillation under a water pump vacuum.

5.2 g (86% of theory) of (S)-(4-chloro-2-methyl-sulphonyl-6-(1-phenyl-ethylamino)-pyrimidine are obtained as a yellowish oily residue.

¹³C-NMR (CDCl₃; 22.6 MHz), δ=22.3 (CH₃), 30.7 (SO₂CH₃), 51.9 (CHCH₃).

STARTING SUBSTANCES OF THE FORMULA (VII)

EXAMPLE (VII-1)

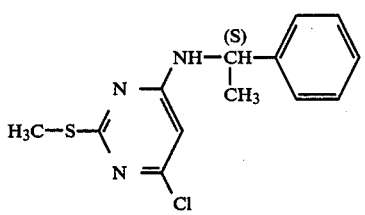

A mixture of 5.9 g (0.03 mol) of 4,6-dichloro-2-methylthio-pyrimidine, 3.1 g (0.031 mol) of triethylamine, 2.7 g (0.031 mol) of (S)-1-phenyl-ethylamine and 80 ml of toluene is refluxed for 12 hours. The mixture is evaporated, and the residue is taken up in methylene chloride, washed with water, dried over sodium sulphate and filtered. The solvent is carefully removed from the filtrate by distillation under a water pump vacuum.

7.0 g (83% of theory) of (S)-4-chloro-2-methylthio-6-(1-phenyl-ethylamino)-pyrimidine are obtained as a yellowish oily residue; NMR spectrum:

$^1$H-NMR (CDCl$_3$, 300 MHz), $\delta = 1.56$ (d, CHCH$_3$); 2.45 (s, SCH$_3$).

USE EXAMPLE

In the following use example the compound of the formula below is employed as comparison substance:

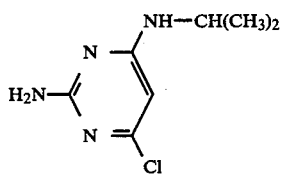

2-Amino-4-chloro-6-isopropylamino-pyrimidine (disclosed in DE-OS (German Published Specification) No. 2,006,145).

EXAMPLE A

Post-emergence test

Solvent: 5 parts by weight of acetone
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction.

In this test, a clearly superior activity compared with the prior art is shown, for example, by the compound according to preparation Example (1).

It will be appreciated that the instant specification and claims are set forth by way of illustration and not limitation, and that various modifications and changes may be made without departing from the spirit and scope of the present invention.

What is claimed is:

1. A pyrimidine derivative of the formula

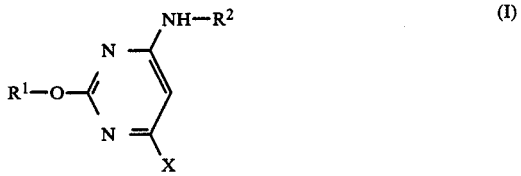

in which
R$^1$ stands for C$_1$–C$_6$-alkyl which is optionally substituted by fluorine, chlorine, bromine, C$_1$–C$_4$-alkoxy (which is optionally substituted by fluorine and/or chlorine), C$_1$–C$_4$-alkoxy-C$_1$–C$_4$-alkoxy, C$_1$–C$_4$-alkylthio, C$_1$–C$_4$-alkylzmino or di(C$_1$–C$_4$-alkyl)-amino,
R$^2$ stands for C$_1$–C$_6$-alkyl which is optionally substituted by fluorine, chlorine, C$_1$–C$_4$-alkoxy, C$_1$–C$_4$-alkylthio, C$_1$–C$_4$-alkylamino or di(C$_1$–C$_4$-alkyl)-amino, for C$_3$–C$_6$-cycloalkyl or C$_3$–C$_6$-cycloalkyl-C$_1$–C$_3$-alkyl which are optionally substituted by fluorine, chlorine, bromine and/or C$_1$–C$_4$-alkyl, or for a radical selected from the group consisting of phenyl, naphthyl, phenyl-C$_1$–C$_4$alkyl, naphthyl-C$_1$–C$_4$-alkyl, pyfidyl, pyridyl-C$_1$–C$_4$-alkyl, quinolinyl, quinolinyl-C$_1$–C$_4$-alkyl, isoquinolinyl, isoquinolinyl-C$_1$–C$_4$-alkyl, pyrimidinyl, pyrimidinyl-C$_1$–C$_4$-alkyl, furyl, furylmethyl, thienyl, thienylmethyl, pyrrolyl, pyrrolyl-C$_1$–C$_4$-alkyl, pyrazolyl, pyrazolyl-C$_1$–C$_4$-alkyl, imidazolyl and imidazolyl-C$_1$–C$_4$-alkyl which is optionally substituted by fluorine, chlorine bromine, iodine, cyano, nitro, C$_1$–C$_4$-alkyl (which is optionally substituted by fluorine and/or chlorine), C$_1$–C$_4$-alkoxy or C$_1$–C$_2$-alkylenedioxy (which are optionally substituted by fluorine and/or chlorine), C$_1$–C$_4$-alkylthio, C$_1$–C$_4$-alkylsulphinyl or C$_1$–C$_4$-alkylsulphonyl (which are optionally substituted by fluorine and/or chlorine), di-(C$_1$–C$_2$-alkyl)-amino and/or by C$_1$–C$_4$-alkoxy-carbonyl, and stands for fluorine, chlorine, bromine, amino, cyanoamino or for a radical from the group consisting of C$_1$–C$_4$-alkoxy, C$_1$–C$_4$-alkylthio, C$_1$–C$_4$-alkylamino and di-(C$_1$–C$_4$-alkyl)-amino which is optionally substituted by fluorine, chlorine, bromine, C$_1$–C$_4$-alkoxy, C$_1$–C$_4$-alkylthio, C$_1$–C$_4$-alkylamino or di-(C$_1$–C$_4$-alkyl)-amino.

2. A pyrimidine derivative according to claim 1, in which
R$^1$ stands for C$_1$–C$_4$-alkyl which is optionally substituted by C$_1$–C$_3$-alkoxy (which is optionally substituted by fluorine) or by C$_1$–C$_3$-alkoxy-C$_1$–C$_3$-alkoxy,
R$^2$ stands for C$_1$–C$_4$-alkyl, C$_3$–C$_6$-cycloalkyl, C$_3$–C$_6$-cycloalkyl-methyl, for phenyl or naphthyl which are optionally substituted by fluorine, chlorine, bromine, cyano, nitro, methyl, ethyl, trifluoromethyl, methoxy and/or ethoxy, for phenyl C$_1$–C$_3$- alkyl or naphthyl-$C_1$-$C_3$-alkyl which are optionally substituted by fluorine, chlorine, bromine, cyano, nitro, methyl, ethyl, trifluoromethyl, methoxy and/or ethoxy, for pyridyl or pyridylmethyl which are optionally substituted by fluorine, chlorine, bromine, cyano, nitro, methyl, ethyl, methoxy and/or ethoxy or for furyl or furylmethyl which are optionally substituted by fluorine, chlorine, bromine, methyl and/or ethyl, and X stands for chlorine, methoxy, ethoxy, methylthio or ethylthio.

3. A pyrimidine derivative according to claim 2, in which $R^1$ stands for $C_1$-$C_2$-alkoxy-$C_1$-$C_3$-alkyl, $R^2$ stands for (R/S)- or (S)-1-phenyl-ethyl which is optionally substituted by fluorine, chlorine, bromine or methyl, and X stands for chlorine.

4. A compound according to claim 2, wherein such compound is (S)-4-chloro-2 (2-ethoxy-ethoxy)-6-(1-phenylethylamino) -pyrimidine of the formula

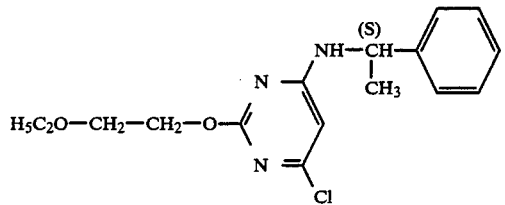

5. A herbicidal composition comprising a herbicidally effective amount of a pyrimidine derivative according to claim 2 and a diluent.

6. A method of combating unwanted vegetation which comprises applying to such vegetation or to a locus from which it is desired to exclude such vegetation a herbicidally effective amount of a pyrimidine derivative according to claim 2.

7. A compound of the formula

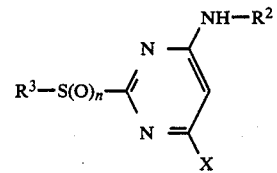

in which $R^2$ is $C_1$-$C_6$-alkyl which is optionally substituted by fluorine, chlorine, $C_1$-$C_4$-alkoxy, $C_1$-$C_4$-alkylthio, $C_1$-$C_4$-alkylamino or di($C_1$-$C_4$-alkyl)-amino, for $C_3$-$C_6$-cycloalkyl or $C_3$-$C_6$-cycloalkyl-$C_1$-$C_3$-alkyl which are optionally substituted by fluorine, chlorine, bromine and/or C-$C_4$-alkyl, or for a radical selected from the group consisting of phenyl, naphthyl, phenyl-$C_1$-$C_4$-alkyl, naphthyl-$C_1$-$C_4$-alkyl, pyridyl, pyridyl-$C_1$-$C_4$-alkyl, quinolinyl, quinolinyl-$C_1$-$C_4$-alkyl, isoquinolinyl, isoquinolinyl-$C_1$-$C_4$-alkyl, pyrimidinyl, pyrimidinyl-$C_1$-$C_4$-alkyl, furyl, furylmethyl, thienyl, thienylmethyl, pyrrolyl, pyrrolyl $C_1$-$C_4$-alkyl, pyrazolyl, pyrazolyl-$C_1$-$C_4$-alkyl, imidazolyl and imidazolyl-$C_1$-$C_4$-alkyl which is optionally substituted by fluorine, chlorine, bromine, iodine, cyano, itro, $C_1$-$C_4$-alkyl (which is optionally substituted by fluorine and/or chlorine), $C_1$-$C_4$-alkoxy or $C_1$-$C_2$-alkylenedioxy (which are optionally substituted by fluorine and/or chlorine), $C_1$-$C_4$-alkylthio, $C_1$-$C_4$-alkylsulphinyl or $C_1$-$C_4$-alkylsulphonyl (which are optionally substituted by fluorine and/or chlorine), di-($C_1$-$C_2$-alkyl)-amino and/or by $C_1$-$C_4$-alkoxy-carbonyl, $R^3$ is methyl or benzyl, n is 0 or 2, and X is fluorine, chlorine, bromine, amino, cyanoamino or for a radical from the group consisting of $C_1$-$C_4$-alkoxy, $C_1$-$C_4$-alkylthio, $C_1$-$C_4$-alkylamino and di-($C_1$-$C_4$-alkyl)-amino which is optionally substituted by fluorine, chlorine, bromine, $C_1$-$C_4$-alkoxy, $C_1$-$C_4$-alkylthio, $C_1$-$C_4$-alkylamino or di-($C_1$-$C_4$-alkyl)amino.

* * * * *

UNITED STATES PATENT AND TRADEMARK OFFICE
CERTIFICATE OF CORRECTION

PATENT NO. : 4,941,910

DATED : July 17, 1990

INVENTOR(S) : Muller et al.

It is certified that error appears in the above-identified patent and that said Letters Patent is hereby corrected as shown below:

| | |
|---|---|
| Title Page | ABSTRACT: Line 8 before " stands " insert -- X -- |
| Col. 24, line 25 | Delete " alkylzmino " and substitute -- alkylamino -- |
| Col. 24, line 34 | Delete " C4alkyl " and substitute -- $C_4$-alkyl -- |
| Col. 24, line 35 | Delete " pyfidyl " and substitute -- pyridyl -- |
| Col. 24, line 50 | Before " stands " insert -- X -- |
| Col. 26, line 16 | Delete " C " and substitute -- $C_1$ -- |
| Col. 26, line 26 | Delete " itro " and substitute -- nitro -- |

Signed and Sealed this

Twelfth Day of May, 1992

Attest:

DOUGLAS B. COMER

*Attesting Officer*  *Acting Commissioner of Patents and Trademarks*